United States Patent
Pelosi, Jr.

[11] 3,966,771
[45] June 29, 1976

[54] 5-(4-CHLOROPHENYL)-2-FURYL KETONES

[75] Inventor: Stanford S. Pelosi, Jr., Norwich, N.Y.

[73] Assignee: Morton-Norwich Products, Inc., Norwich, N.Y.

[22] Filed: June 16, 1975

[21] Appl. No.: 586,877

[52] U.S. Cl. ................... 260/347.8; 424/285
[51] Int. Cl.² ........................... C07D 307/46
[58] Field of Search ..................... 260/347.8

[56] References Cited
UNITED STATES PATENTS
3,801,605  4/1974  Carson ..................... 260/347.5

OTHER PUBLICATIONS
Buer–Hoi et al., Chem. Abst., vol. 45, col. 7104–7105, (1951).
Tsichiya, Chem. Abst., vol. 59, col. 2751, (1963).

Primary Examiner—Harry I. Moatz
Attorney, Agent, or Firm—Anthony J. Franze

[57] ABSTRACT

Certain 5-(4-chlorophenyl)-2-furyl ketones of the formula:

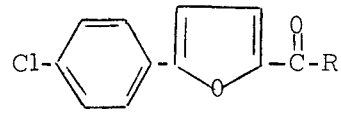

wherein R is cyclopropyl or 2-furyl are effective anthelmintic agents.

3 Claims, No Drawings

5-(4-CHLOROPHENYL)-2-FURYL KETONES

This invention relates to chemical compounds. More particularly this invention relates to certain 5-(4-chlorophenyl)-2-furyl ketones of the formula:

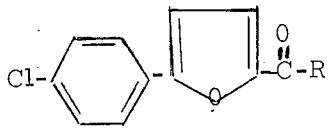

wherein R is cyclopropyl or 2-furyl and a method for their preparation.

These compounds are distinguished by their ability to combat helminth infection. When administered by gavage as a suspension in aqueous solution to mice harboring *Nematospiroides dubius* worms, these compounds, in a dose ranging from 50–300 mg/kg, accomplish a 44–88% reduction of the worm burden.

The compounds of this invention are readily prepared. Currently it is preferred to react the appropriate acyl chloride with 2-(4-chlorophenyl)furan in the presence of aluminum chloride and carbon disulfide. In order that this invention may be fully available to and understood by those skilled in the art, the following examples are supplied.

EXAMPLE I

5-(4-chlorophenyl)-2-furyl Cyclopropyl Ketone

To a stirring mixture of 128 g (0.96 mole) of $AlCl_3$ and 720 ml of $CS_2$ was added portionwise 100 g (0.96 mole) of cyclopropanecarboxylic acid chloride while keeping the temperature below 30° by means of an ice bath. A solution of 172 g (0.96 mole) of 2-(4-chlorophenyl)furan in 480 ml of $CS_2$ was added dropwise while maintaining the temperature between 10°–15° with large volume of HCl gas being given off. The reaction mixture was stirred in an ice bath for 15 minutes, allowed to warm to room temperature over a one hour period, and then added to 2000 ml of ice/water. The aqueous layer was separated from the $CS_2$ layer and extracted with 2 × 500 ml portions of $CH_2Cl_2$. The $CS_2$ and $CH_2Cl_2$ layers were combined, were washed with 1000 ml of 6% $Na_2CO_3$ solution and with 1000 ml of water, and then dried over magnesium sulfate. The solvent was removed on a rotary evaporator leaving red-brown residue which was extracted several times with boiling hexane. The combined hexane extracts were cooled and the resulting solid filtered and air dried to yield 41 g (17%) of product. An analytical sample was prepared by recrystallizing a sample from hexane/Darco, m.p. 88°–89°.

Anal. Calcd. for $C_{14}H_{11}ClO_2$: C, 68.16; H, 4.49. Found: C, 68.20; H, 4.49.

EXAMPLE II

5-(4-Chlorophenyl)-2-furyl 2-Furyl Ketone

To a mixture of 113 g (1.0 mole) of $AlCl_3$ in 750 ml of $CS_2$ was added carefully 130 g (1.0 mole) of 2-furoyl chloride. A solution of 178 g (1.0 mole) of 2-(4-chlorophenyl)furan in 500 ml of $CS_2$ was added dropwise while maintaining the temperature at 15°–20° by means of an ice bath. The reaction mixture was kept at 15°–20° for 30 minutes, at room temperature for 30 minutes and then added to 2000 ml of ice/water. The aqueous layer was separated from the $CS_2$ layer and extracted with 2 × 500 ml portions of $CH_2Cl_2$. The $CS_2$ and $CH_2Cl_2$ layers were combined and washed with 1000 ml of 6% $Na_2CO_3$ solution, with 1000 ml of water and dried over $MgSO_4$. The solvent was removed on a rotary evaporator leaving a residual oil which was distilled under reduced pressure to yield 20 g of oil which solidified on cooling, b.p. >250° at 1–5 mm. This solid was dissolved in refluxing hexane, treated with Darco, filtered, and cooled to room temperature with the resulting solid being filtered and air dried to yield 5.5 g (2%). An analytical sample was prepared by drying a sample in the vacuum pistol at the temperature of refluxing $CHCl_3$, m.p. 121°–122°.

Anal. Calcd. for $C_{15}H_9ClO_3$: C, 66.07; H, 3.33. Found: C, 66.09; H, 3.47.

What is claimed is:

1. A compound of the formula:

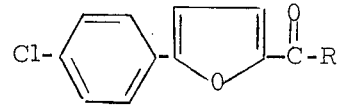

wherein R is cyclopropyl or 2-furyl.

2. The compound 5-(4-chlorophenyl)-2-furyl cyclopropyl ketone.

3. The compound 5-(4-chlorophenyl)-2-furyl 2-furyl ketone.

* * * * *